United States Patent
Oyama

(10) Patent No.: US 12,042,339 B2
(45) Date of Patent: Jul. 23, 2024

(54) MEDICAL SYSTEM AND METHOD OF CONTROLLING MEDICAL SYSTEM

(71) Applicant: OLYMPUS CORPORATION, Tokyo (JP)

(72) Inventor: Masatsugu Oyama, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 925 days.

(21) Appl. No.: 17/038,152

(22) Filed: Sep. 30, 2020

(65) Prior Publication Data

US 2021/0113057 A1  Apr. 22, 2021

Related U.S. Application Data

(63) Continuation of application No. PCT/JP2019/004613, filed on Feb. 8, 2019.

(30) Foreign Application Priority Data

Apr. 10, 2018  (JP) .................................. 2018-075400

(51) Int. Cl.
  *A61B 1/00*   (2006.01)
  *A61B 90/00*  (2016.01)

(52) U.S. Cl.
  CPC .......... *A61B 90/37* (2016.02); *A61B 1/00006* (2013.01); *A61B 1/00009* (2013.01);
  (Continued)

(58) Field of Classification Search
  CPC .............. A61B 1/0004; A61B 1/00006; A61B 1/00009; A61B 1/0002; A61B 1/00045; A61B 90/37; A61B 2090/062
  See application file for complete search history.

(56) References Cited

U.S. PATENT DOCUMENTS

2006/0009679 A1  1/2006 Ito et al.
2006/0106284 A1  5/2006 Shouji et al.
(Continued)

FOREIGN PATENT DOCUMENTS

CN  105848559 A    8/2016
EP    3100668 A1  12/2016
(Continued)

OTHER PUBLICATIONS

International Search Report dated Apr. 23, 2019 issued in PCT/JP2019/004613.

*Primary Examiner* — Timothy J Neal
*Assistant Examiner* — William B Chou
(74) *Attorney, Agent, or Firm* — Scully, Scott, Murphy & Presser, P.C.

(57) ABSTRACT

A medical system includes: an endoscope including an insertion portion inserted into a subject, an image pickup device configured to output an image signal of the subject being arranged in the insertion portion; a video processor configured to process the image signal to generate image data; an insertion length acquisition apparatus configured to acquire information on an insertion length when the insertion portion of the endoscope is inserted into the subject; and an image recording apparatus including a storage device configured to record the image data as a moving image. The image recording apparatus includes an image generation apparatus configured to edit the moving image and generate a moving image for saving, based on the information on the insertion length supplied from the insertion length acquisition apparatus.

20 Claims, 14 Drawing Sheets

(52) U.S. Cl.
CPC .......... *A61B 1/0002* (2013.01); *A61B 1/0004* (2022.02); *A61B 1/00045* (2013.01); *A61B 2090/062* (2016.02)

(56) References Cited

U.S. PATENT DOCUMENTS

| | | | |
|---|---|---|---|
| 2010/0113876 | A1 | 5/2010 | Ishihara |
| 2012/0078045 | A1 | 3/2012 | Sasaki et al. |
| 2016/0242625 | A1 | 8/2016 | Kumagai et al. |
| 2016/0323514 | A1 | 11/2016 | Tsuchiya et al. |
| 2017/0360285 | A1 | 12/2017 | Yamada |
| 2018/0242818 | A1* | 8/2018 | Kubo .................... A61B 1/005 |
| 2022/0198742 | A1* | 6/2022 | Nishide .................... G06T 7/70 |
| 2023/0380913 | A1* | 11/2023 | Ida ........................ A61B 34/37 |

FOREIGN PATENT DOCUMENTS

| | | |
|---|---|---|
| JP | H08-313823 A | 11/1996 |
| JP | 2004-350734 A | 12/2004 |
| JP | 2005-312770 A | 11/2005 |
| JP | 2006-020873 A | 1/2006 |
| JP | 2006-043449 A | 2/2006 |
| JP | 2008-220672 A | 9/2008 |
| JP | 2011-15109 A | 1/2011 |
| JP | 2012-070938 A | 4/2012 |
| JP | 2012-120706 A | 6/2012 |
| JP | 2015-107268 A | 6/2015 |
| JP | 2016-007444 A | 1/2016 |
| JP | 2016-043033 A | 4/2016 |
| JP | 2016-171946 A | 9/2016 |
| JP | 2017-108792 A | 6/2017 |
| JP | 2018-007960 A | 1/2018 |
| JP | 2018-047088 A | 3/2018 |
| WO | WO 2004/103167 A1 | 12/2004 |
| WO | WO 2008/111646 A1 | 9/2008 |
| WO | WO 2015/114901 A1 | 8/2015 |
| WO | WO 2015/182674 A1 | 12/2015 |
| WO | WO 2015/190435 A1 | 12/2015 |
| WO | WO 2016/147778 A1 | 9/2016 |
| WO | WO 2018/055950 A1 | 3/2018 |

* cited by examiner

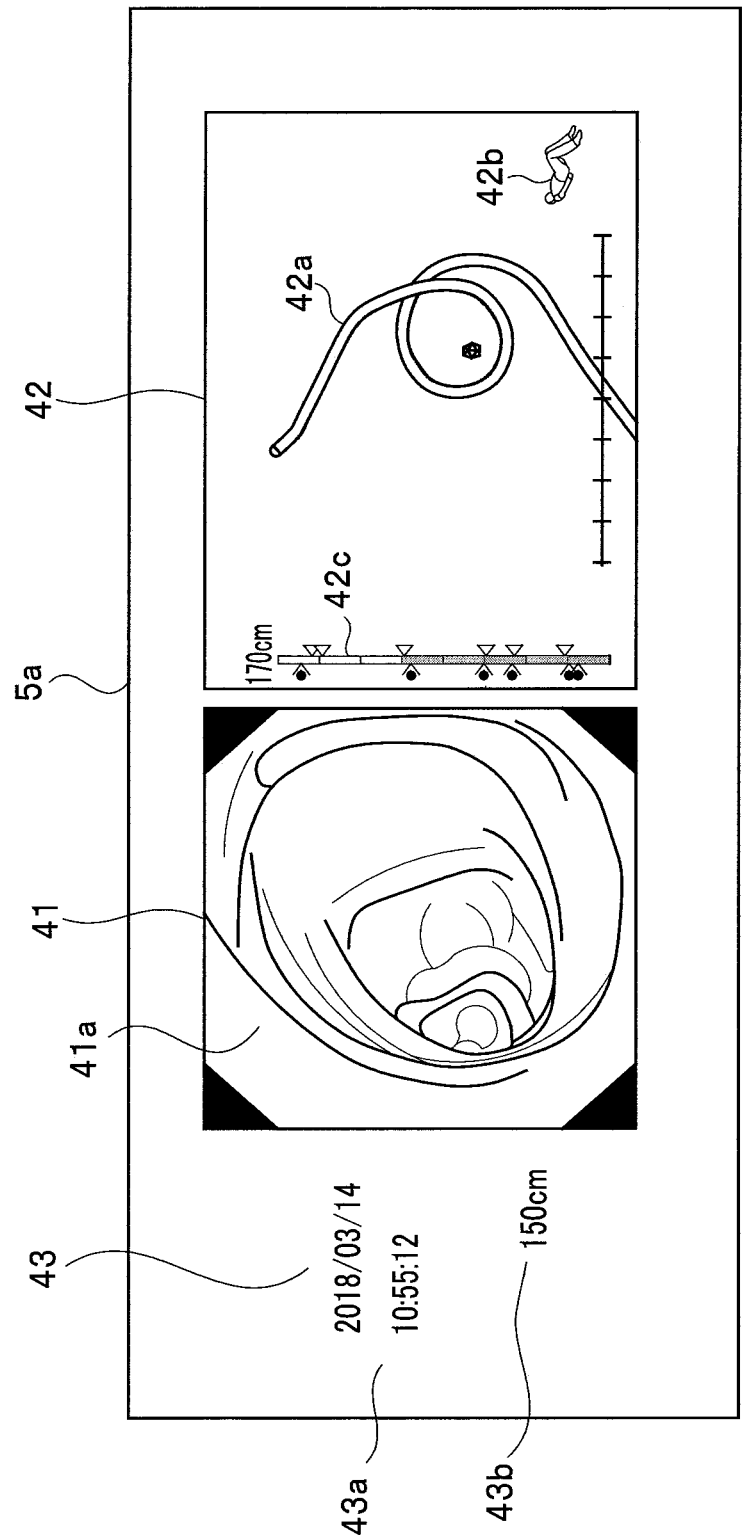

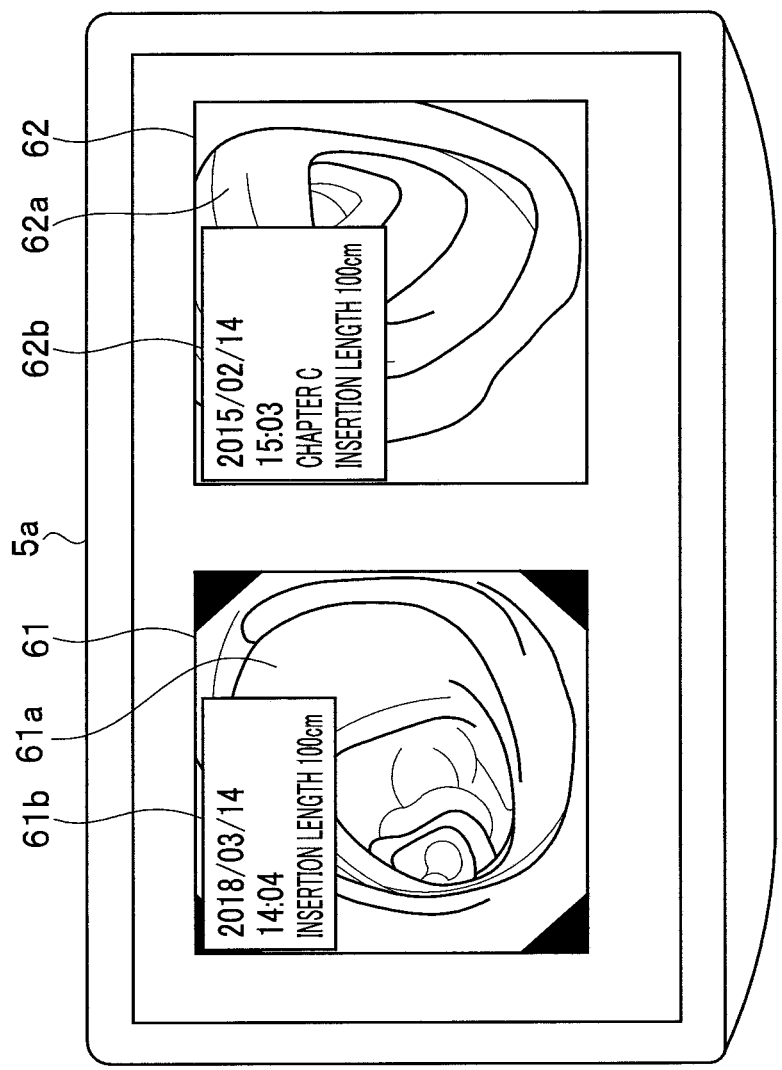

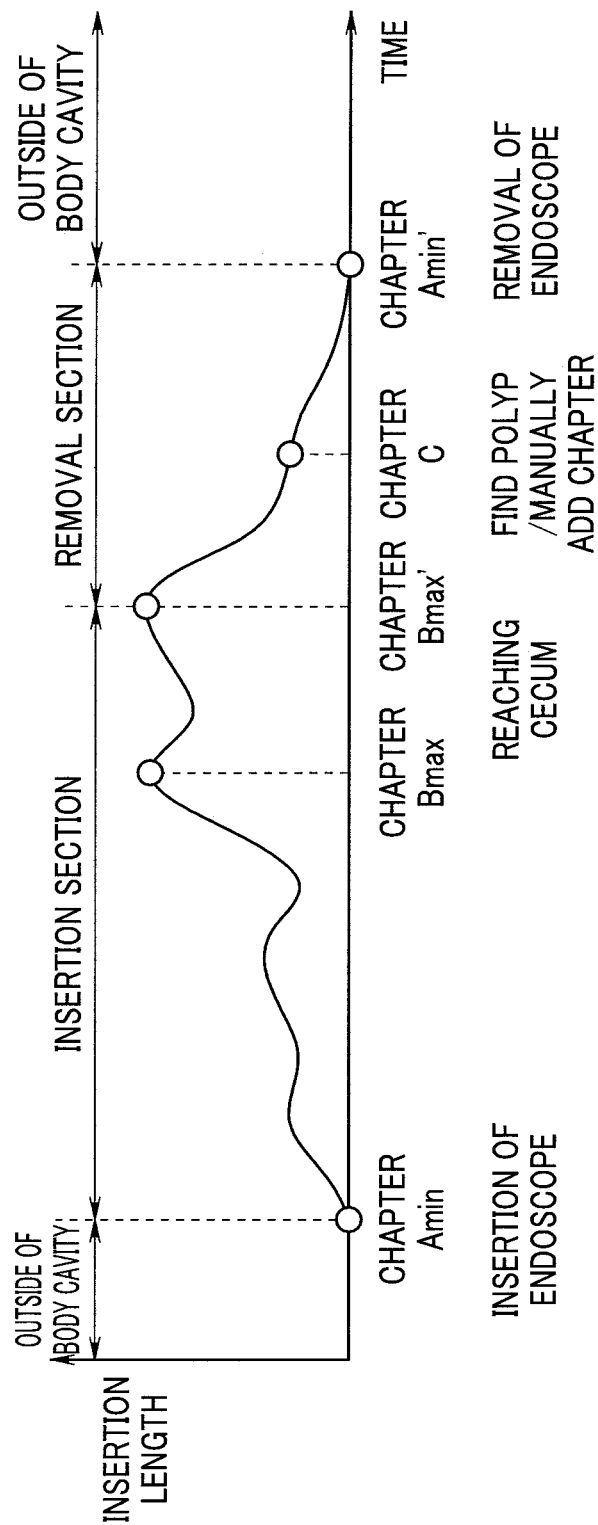

MEDICAL SYSTEM AND METHOD OF CONTROLLING MEDICAL SYSTEM

CROSS REFERENCE TO RELATED APPLICATION

This application is a continuation application of PCT/JP2019/004613 filed on Feb. 8, 2019 and claims benefit of Japanese Application No. 2018-075400 filed in Japan on Apr. 10, 2018, the entire contents of which are incorporated herein by this reference.

BACKGROUND OF THE INVENTION

1. Field of the Invention

The present invention relates to a medical system that records an endoscope image and information on an insertion length of an endoscope in association with each other, and a method of controlling the medical system.

2. Description of the Related Art

Conventionally, an endoscope apparatus has been widely used in a medical field. The endoscope apparatus is a medical instrument including an elongated insertion portion having flexibility, and an operator can insert the insertion portion into a subject and can observe the inside of the subject. An endoscope image of the inside of the subject picked up by an endoscope can be displayed on a monitor. However, it is not possible to know how the insertion portion of the endoscope is inserted into the subject from the endoscope image.

Therefore, as an apparatus that can know an insertion state of the endoscope at the time of insertion of the endoscope, an endoscope shape observation apparatus has been developed which includes a plurality of transmission coils incorporated in the insertion portion, a receiving antenna formed by a plurality of sense coils arranged in a coil block, and a monitor on which an insertion shape of the insertion portion is displayed. For example, various endoscope shape observation apparatuses disclosed in Japanese Patent Application Laid Open Publication No. 2005-312770 have been proposed.

By the way, medical images obtained by the endoscope are recorded in various media for diagnosis and record of medical cases. In recent years, as the capacity of recording medium has increased, moving images from the endoscope have also been recorded. For the purpose of recording the medical cases, it is conceivable to use the medical images as backups for evidence images or the like and to use the medical images as educational materials. Furthermore, comparison of a past medical case moving image with a current moving image of the same patient may be effective at the time of follow-up observation.

However, even when a whole period of the medical case is recorded, a procedure or only an image at a part of an examination period may be required depending on purpose of use, and editing work may be performed after the recording of the medical case. For example, only a moving image of a part of the body cavity may be recorded as necessary.

SUMMARY OF THE INVENTION

A medical system according to an aspect of the present invention includes: an endoscope including an insertion portion inserted into a subject, an image pickup device configured to output an image signal of the subject being arranged in the insertion portion; a video processor configured to process the image signal to generate image data; an insertion length acquisition apparatus configured to acquire information on an insertion length when the insertion portion of the endoscope is inserted into the subject; and an image recording apparatus including a storage device configured to record the image data as a moving image, wherein the image recording apparatus includes an image generation apparatus configured to edit the moving image and generate a moving image for saving, based on the information on the insertion length supplied from the insertion length acquisition apparatus.

A method of controlling a medical system according to another aspect of the present invention includes: acquiring, when an endoscope is inserted into a subject, information on an insertion length of an inserted endoscope from an insertion length acquisition apparatus; receiving an image signal of the subject picked up by the inserted endoscope when acquiring the information; and recording an endoscope moving image generated by processing the image signal and the information on the insertion length in a storage device in association with each other, wherein the endoscope moving image recorded in the storage device is read out, and an unnecessary part is deleted based on the information on the insertion length, and a remaining part is saved in the storage device as a moving image for saving.

BRIEF DESCRIPTION OF THE DRAWINGS

FIG. 4 is an explanatory diagram showing an example in which a playback image is displayed;

FIG. 13 is an explanatory diagram showing an example in which an image is displayed on a monitor 5; and FIG. 14 is an explanatory diagram illustrating a modification.

DETAILED DESCRIPTION OF THE PREFERRED EMBODIMENTS

Embodiments of the present invention will be described below in detail with reference to the drawings.

First Embodiment

Figure 1:
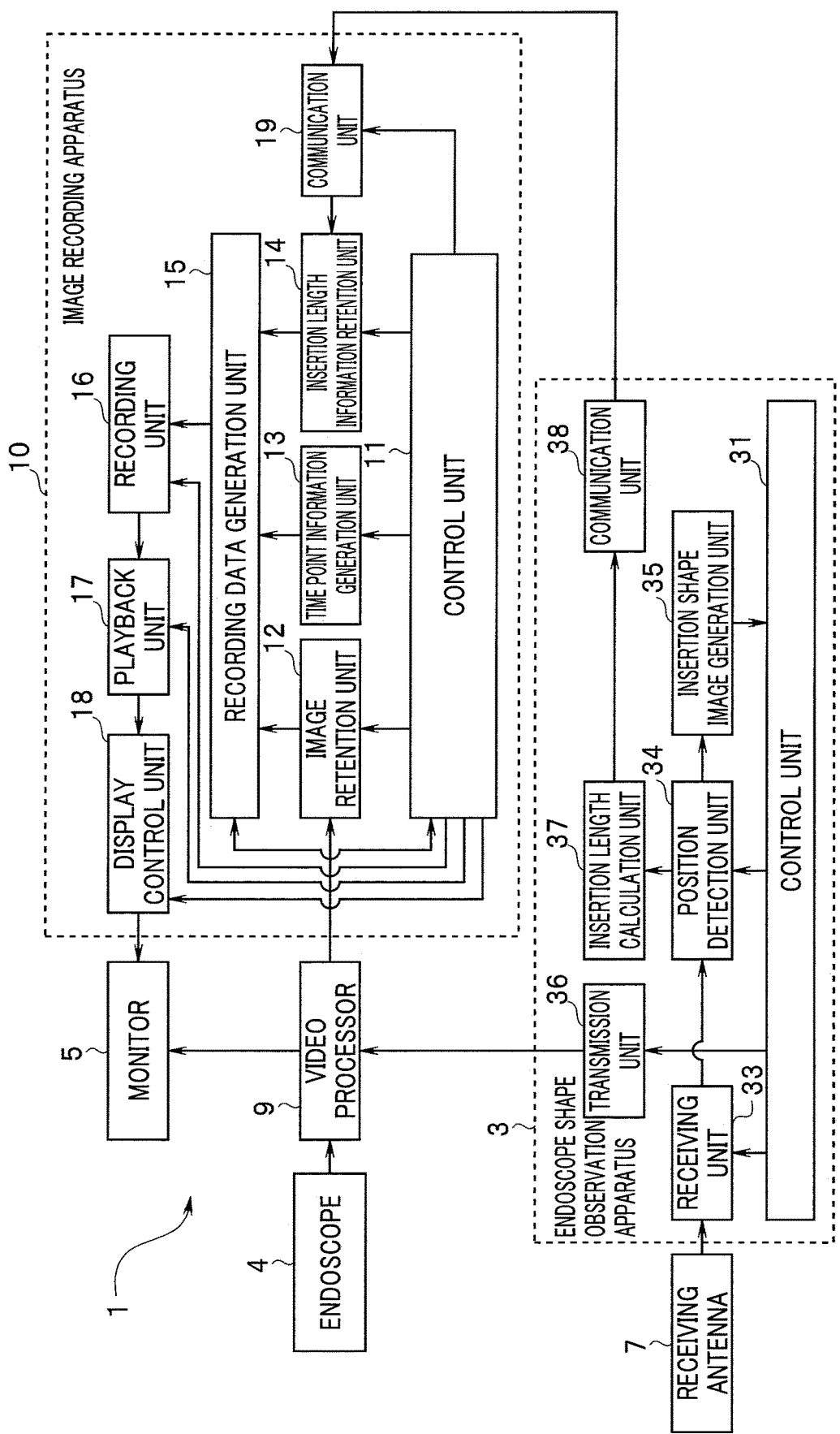
FIG. 1 is a block diagram showing a medical system according to a first embodiment of the present invention.
Figure 2:
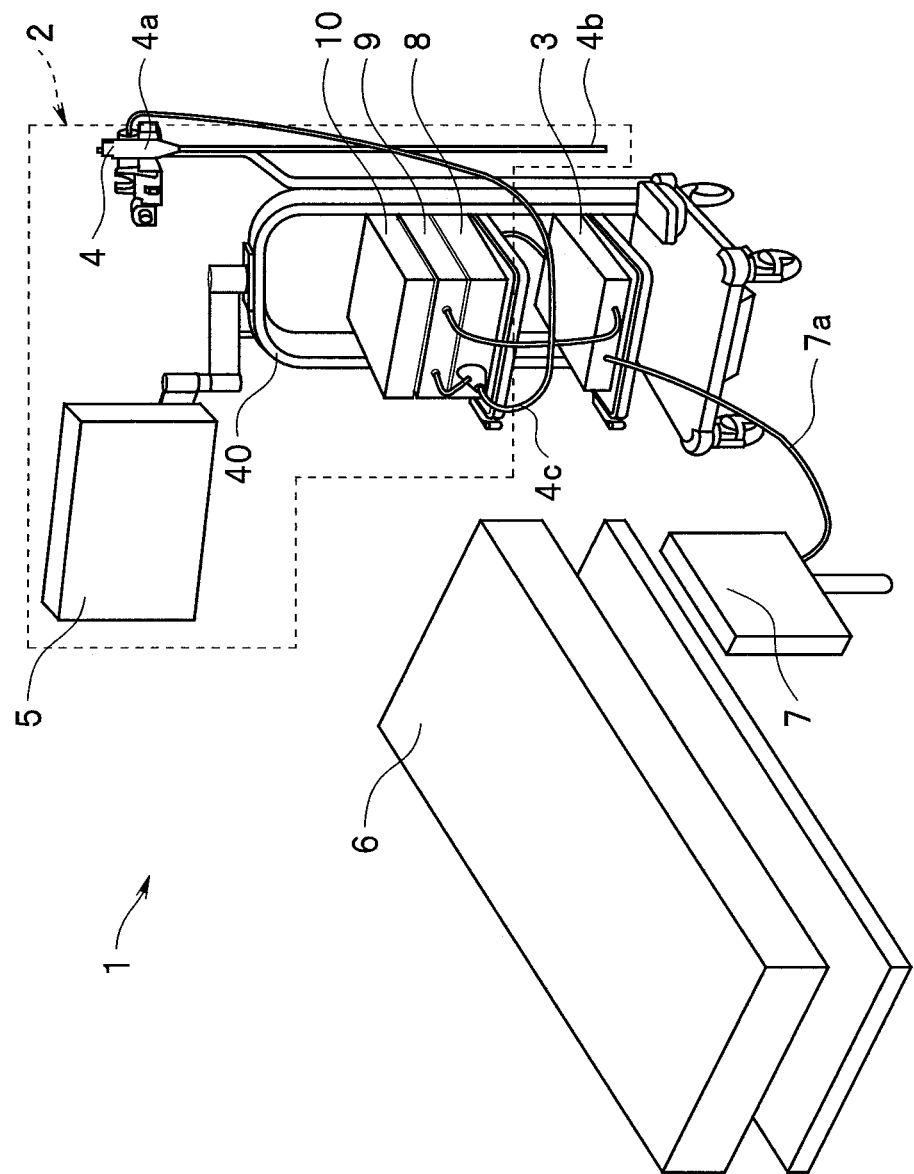
FIG. 2 is an explanatory diagram showing an example in which a medical system is arranged in an operating room.

FIG. 1 is a block diagram showing a medical system according to a first embodiment of the present invention. FIG. 2 is an explanatory diagram showing an example of arrangement of the medical system in an operating room. In addition, FIG. 3 is an explanatory diagram showing a state of an endoscope examination.

The present embodiment is to record information indicating at which position in a body cavity an endoscope image is observed, using an endoscope shape observation apparatus configured to observe an insertion shape of an endoscope, for example, to record insertion length information indicating a length of the endoscope insertion portion inserted into the body cavity (hereinafter, referred to as an insertion length) in association with the endoscope image. Thus, the observation position indicated by the endoscope image can be easily recognized at the time of editing the endoscope image, referring to a past medical case during follow-up observation or the like.

Figure 3:
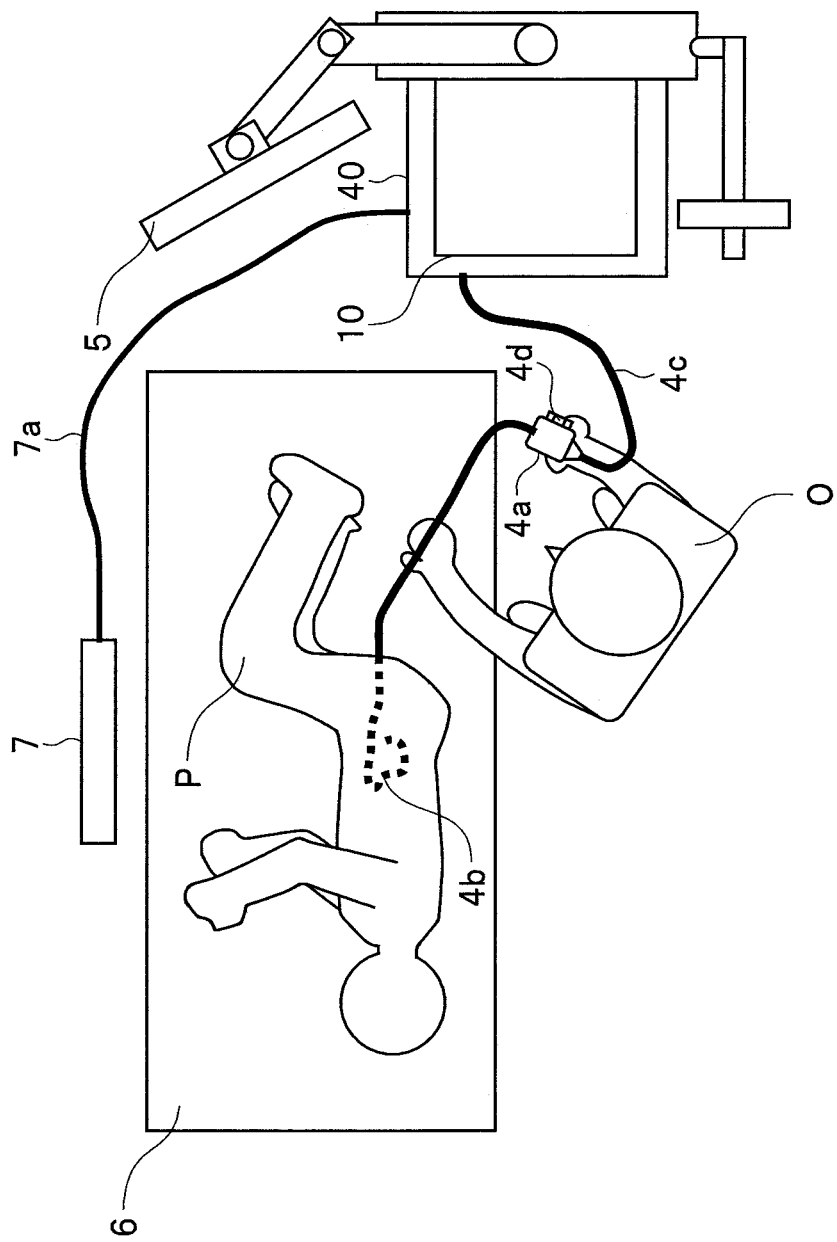
FIG. 3 is an explanatory diagram showing a state of an endoscope examination.

In FIGS. 2 and 3, a medical system 1 includes an endoscope apparatus 2, an endoscope shape observation apparatus 3, and an image recording apparatus 10. The endoscope apparatus 2 includes an endoscope 4, a light source apparatus 8, a video processor 9, and a monitor 5. The endoscope 4 includes an elongated insertion portion 4b that is inserted into a body cavity of a subject P, which is a subject, and has flexibility, an operation portion 4a that is connected to a proximal end of the insertion portion 4b and is provided with various operation instruments, and a cable 4c used to connect the operation portion 4a and the video processor 9.

FIG. 2 shows an example in which the endoscope shape observation apparatus 3, the image recording apparatus 10, the light source apparatus 8, and the video processor 9 are mounted on a medical trolley 40. In addition, the monitor 5 is attached to a movable arm provided in the medical trolley 40. The endoscope 4 can be hooked on a hook of the medical trolley 40.

FIG. 3 shows a state in which the insertion portion 4b is inserted into a large intestine from an anus of the subject P lying on a bed for examination 6. FIG. 3 shows a state in which an operator 0 is grasping the operation portion 4a and the insertion portion 4b of the endoscope 4 connected to the video processor 9 on the medical trolley 40 by the cable 4c.

The light source apparatus 8 generates illuminating light for illuminating the subject. The illuminating light generated by the light source apparatus 8 is guided to a distal end portion of the insertion portion 4b by a light guide (not shown) inserted into the insertion portion 4b of the endoscope 4, and is irradiated to the subject from the distal end portion of the insertion portion 4b. An image pickup device (not shown) is arranged at the distal end portion of the insertion portion 4b, and reflected light (return light) reflected from the subject forms an image, as an optical image of an object, on a light receiving surface of the image pickup device. The image pickup device is controlled to be driven by the video processor 9, thereby converting the optical image of the object into an image signal and outputting the image signal to the video processor 9. The video processor 9 includes an image signal processing unit (not shown), and the image signal processing unit receives the image signal from the image pickup device, performs signal processing, and outputs an endoscope image subjected to the signal processing to the monitor 5. In this way, the endoscope image of the subject is displayed on a display screen of the monitor 5.

A bending portion is provided at the distal end of the insertion portion 4b, and the bending portion is driven to be bent by a bending knob 4d provided on the operation portion 4a. The operator can bend the bending portion and push the insertion portion 4b into the body cavity by operating the bending knob 4d.

An insertion state of the insertion portion 4b is observed by the well-known endoscope shape observation apparatus 3. A plurality of transmission coils are arranged in the insertion portion 4b to detect an insertion state. For example, the plurality of transmission coils are arranged at predetermined intervals in an axial direction in the insertion portion 4b. For example, a probe, to which the plurality of transmission coils are attached at predetermined intervals, may be inserted into a treatment instrument insertion channel and a distal end or a rear end of the probe may be fixed.

On the other hand, a receiving antenna 7 is arranged near the bed 6. The receiving antenna 7 is connected to the endoscope shape observation apparatus 3 by a cable 7a. The receiving antenna 7 includes a plurality of coil blocks (not shown), and is arranged on a side of the bed 6, for example. Each of the coil blocks of the receiving antenna 7 is configured by three sense coils, which are respectively wound in three directions and have coil surfaces orthogonal to each other, respectively, and four coil blocks, that is, 12 sense coils are arranged in the receiving antenna 7 in total, for example. Each of the sense coils is configured to detect a signal proportional to strength of a magnetic field of an axial direction component orthogonal to the coil surface of the sense coil. For example, the coil block is configured to receive the generated magnetic field, convert the magnetic field into a voltage signal, and output the voltage signal as a detection result. The operating state of the transmission coil and the receiving antenna 7 provided in the insertion portion 4b is controlled by the endoscope shape observation apparatus 3.

As shown in FIG. 1, the endoscope shape observation apparatus 3 includes a control unit 31. The control unit 31 may be configured by a processor using a CPU or the like and operate according to a program stored in a memory (not shown) to control each of units, or may realize a part or all of functions in a hardware electronic circuit. The control unit 31 controls overall the endoscope shape observation apparatus 3.

The control unit 31 gives sinusoidal signals for driving the plurality of transmission coils provided in the insertion portion 4b to the respective transmission coils (not shown). Each of the transmission coils provided in the insertion portion 4b radiates an electromagnetic wave accompanied by a magnetic field to the surroundings by applying of a high-frequency sinusoidal wave. The endoscope shape observation apparatus 3 can sequentially drive each of the transmission coils at appropriate time intervals, for example, at intervals of several milliseconds (ms).

The receiving antenna 7 receives the magnetic field, which is generated by the transmission coils, using the sense coils and converts the magnetic field into a voltage signal. The receiving antenna 7 gives the voltage signal as a detection result to a receiving unit 33 of the endoscope shape observation apparatus 3. The receiving unit 33 receives a signal from the receiving antenna 7, and outputs the signal to a position detection unit 34 after performing predetermined signal processing such as amplification processing on the signal.

The position detection unit 34 is configured by, for example, a DSP, and is configured to perform frequency extraction processes (Fourier transform: FFT) on the inputted digital data to separate and extract magnetic field detection information of a frequency component corresponding to a high-frequency sinusoidal wave of each of the transmission coils, and to calculate spatial position coordinates of each of the transmission coils from each of the digital data of the separated magnetic field detection information. A calculation result of the position coordinates by the position detection unit 34 is supplied to an insertion shape image generation unit 35. The insertion shape image generation unit 35 connects position coordinates of each of the transmission coils to generate a linear image as an insertion shape image.

The insertion shape image generation unit 35 gives the generated insertion shape image to the control unit 31. The control unit 31 converts the insertion shape image generated by the insertion shape image generation unit 35 into display data for displaying on the monitor 5 and gives the display data to a transmission unit 36. The transmission unit 36 transmits the inputted display data to the video processor 9. The video processor 9 combines the endoscope image inputted from the endoscope 4 and the insertion shape image as the display data given from the endoscope shape observation apparatus 3, and gives the combined image to the monitor 5. The monitor 5 can be configured by, for example, an LCD, and displays, based on the output of the video processor 9, the endoscope image and the insertion shape image based on a relative positional relation between the transmission coils and the receiving antenna 7 at the same time.

The insertion shape image generated by the insertion shape image generation unit 35 is generated using a coordinate system (hereinafter, referred to as a measurement coordinate system) based on the position of the receiving antenna 7. The control unit 31 performs a coordinate conversion to display the insertion shape image at a predetermined position on the display screen of the monitor 5. In other words, the control unit 31 performs a coordinate conversion on the inputted image to convert the measurement coordinate system into a display coordinate system. By such a coordinate conversion of the control unit 31, the insertion shape image can be displayed at a predetermined position on the display screen of the monitor 5 with a predetermined orientation and size. The display position, orientation, and size of the insertion shape image can be changed by the operator's operation.

The endoscope shape observation apparatus 3 as an insertion length acquisition apparatus is provided with an insertion length calculation unit 37. The insertion length calculation unit 37 calculates a length of the insertion portion 4b inserted into the body cavity. Assuming that a predetermined transmission coil of the transmission coils is located at the anal position (insertion position) of the subject P after the insertion portion 4b is inserted into the subject P, the insertion portion 4b is inserted into the body cavity up to the distal end from the position of the predetermined coil. The position of each of the transmission coils inserted into the insertion portion 4b from the distal end of the insertion portion 4b is known. Accordingly, when the coil located at the anal position is detected, the length (insertion length) of the insertion portion 4b inserted into the body cavity can be obtained.

In addition, various methods of detecting the anal position can be considered. Examples of the methods include a method of locating the anus of the subject P at a prescribed position with respect to the receiving antenna 7, a method of arranging a marker including a built-in transmission coil near the anus and receiving a magnetic field generated by a high-frequency sinusoidal wave applied to the marker using the receiving antenna 7, or a method of detecting a position of the coil arranged at the distal end of the insertion portion 4b at the start of insertion of the insertion portion 4b into the anus.

The insertion length calculation unit 37 receives information on the anal position coordinates and information on the position coordinates of each of the coils provided in the insertion portion 4b, which is inserted currently, from the position detection unit 34. The insertion length calculation unit 37 detects a coil located near the anal position coordinates among the coils, and calculates the length from the position of the coil to the distal end of the insertion portion 4b, as the insertion length. The insertion length calculation unit 37 sequentially updates the insertion length based on the output of the position detection unit 34, and gives the insertion length information to a communication unit 38. The communication unit 38 transmits the inputted insertion length information to the image recording apparatus 10.

By giving the insertion length information inputted from the insertion length calculation unit 37 to the control unit 31, the transmission unit 36 may transmit the insertion length information to the video processor 9 together with the insertion shape image. In this case, the video processor 9 can also generate an endoscope image during observation, an insertion shape image, and an image including a display of the insertion length.

The image recording apparatus 10 includes a control unit 11. The control unit 11 may be configured by a processor using a CPU or the like and operate according to a program stored in a memory (not shown) to control each of units, or may realize a part or all of functions in a hardware electronic circuit. An endoscope image is supplied to the image recording apparatus 10 from the video processor 9. An image retention unit 12 of the image recording apparatus 10 is configured to retain the endoscope image supplied from the video processor 9, and to output the retained endoscope image to a recording data generation unit 15 under control of the control unit 11. An example of the image outputted from the video processor 9 may include only the endoscope image, or the combined image of the endoscope image and the insertion shape image. In order to simplify the description below, the endoscope image may include both the images described above.

The image recording apparatus 10 includes a communication unit 19. The communication unit 19 communicates with the communication unit 38 of the endoscope shape observation apparatus 3 to receive the insertion length information from the endoscope shape observation apparatus 3 and to give the insertion length information to an insertion length information retention unit 14. The insertion length information retention unit 14 is configured to retain the insertion length information and output the retained insertion length information to the recording data generation unit 15 under control of the control unit 11. In addition, a time point information generation unit 13 of the image recording apparatus 10 is controlled by the control unit 11 to generate time point information, and outputs the generated time point information to the recording data generation unit 15.

The recording data generation unit 15 receives the endoscope image from the image retention unit 12, receives the time point information from the time point information generation unit 13, and receives the insertion length information from the insertion length information retention unit 14. In the endo scope image, a time from the start of recording is specified by the time point information. The recording data generation unit 15 records the insertion length information at each recording time of the endoscope image, as metadata, in association with the endoscope image. In other words, the recording data generation unit 15 is configured to record the endoscope image and the insertion length information in a recording unit 16 in association with each other using the time point information.

For example, the recording data generation unit 15 may be configured to generate an image file configured by the image data based on the endoscope image and the metadata based on the time point information and the insertion length information. The recording data generation unit 15 is controlled by the control unit 11 to give the generated image file to the recording unit 16 for recording.

Examples of the recording unit 16 as a storage device may include various recording media such as a hard disk or an IC memory. Further, examples of the recording unit 16 may include not only the recording unit built in the image recording apparatus 10 but also various storages such as various disk media, USB memories, or file servers on a network.

A playback unit 17 as a playback apparatus can read and play back the image file recorded in the recording unit 16. The playback unit 17 reads the playback endoscope image and the metadata associated with the endoscope image from the recording unit 16, and outputs the endoscope image and the metadata to a display control unit 18 as a display control circuit.

The display control unit 18 can receive the insertion length information included in the endoscope image and the metadata from the playback unit 17 and cause the monitor 5 to receive and display an image including a display (insertion length display) based on the insertion length information and the endoscope image. The display control unit 18 can be controlled by the control unit 11 to cause the monitor 5 to display the endoscope image including the insertion length display on the display screen in various forms.

The monitor 5 can also be configured to combine and display the image outputted from the video processor 9 and the image outputted from the image recording apparatus 10. For example, the monitor 5 can display the image outputted from the video processor 9 and the image outputted from the image recording apparatus 10 on two screens.

Figure 5A:
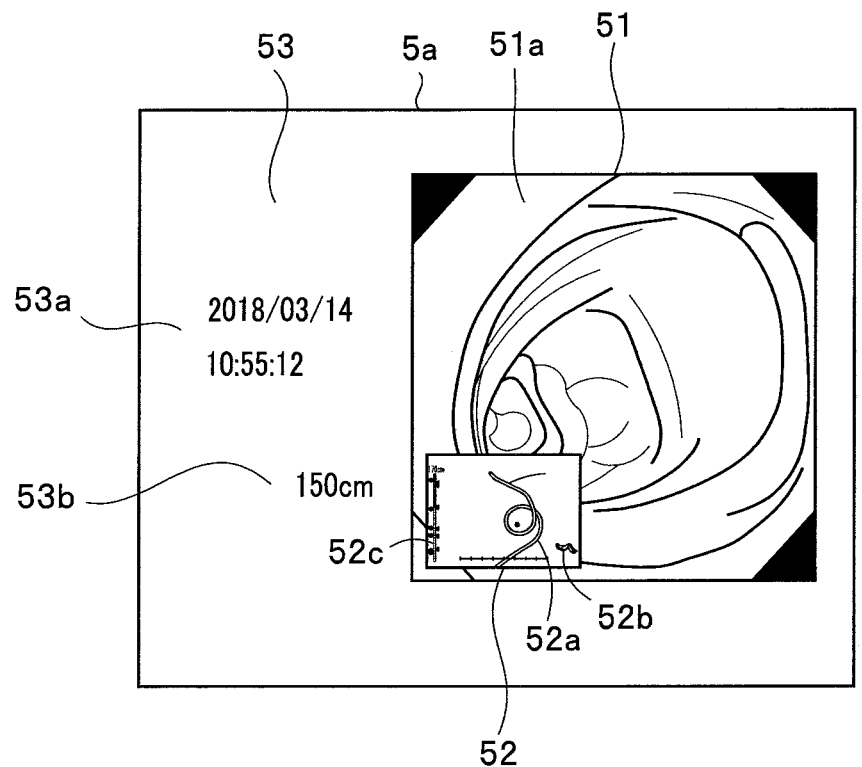
FIG. 5A is an explanatory diagram showing an example in which a playback image is displayed.
Figure 5B:
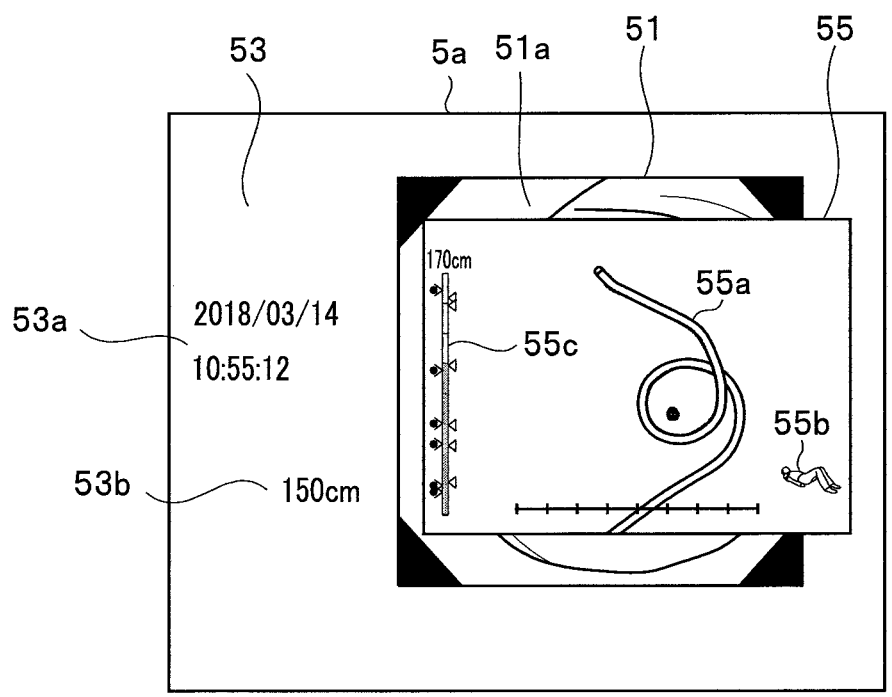
FIG. 5B is an explanatory diagram showing an example in which a playback image is displayed.

Next, an operation of the embodiment configured in this way will be described with reference to FIGS. 4, 5A, and 5B. FIGS. 4, 5A, and 5B are explanatory diagrams showing examples in which a playback image is displayed.

As shown in FIG. 3, the operator inserts the insertion portion 4b into the large intestine of the anus of the subject P lying on the bed for examination 6 in a lateral decubitus position. The endoscope shape observation apparatus 3 obtains three-dimensional position coordinates of the plurality of transmission coils built in the insertion portion 4b at predetermined time intervals. In other words, the control unit 31 of the endoscope shape observation apparatus 3 supplies high-frequency signals to the plurality of transmission coils of the insertion portion 4b at predetermined timings. The transmission coil supplied with the high-frequency signal generates an electromagnetic wave accompanied by a magnetic field. Such a magnetic field is received by each of the coil blocks of the receiving antenna 7, and a detection result according to magnetic field strength is taken into the position detection unit 34 via the receiving unit 33 of the endoscope shape observation apparatus 3.

The position detection unit 34 receives information on a drive timing of each of the transmission coils from the control unit 31 to obtain a three-dimensional position coordinates of each of the transmission coils based on the detection result of the coil block for each of the transmission coils, according to a known position estimation algorithm. Such position coordinates are supplied to the insertion shape image generation unit 35, and the insertion shape image generation unit 35 generates an insertion shape image based on the position coordinates. The respective transmission coils are arranged at known positions with predetermined intervals along the shape of the insertion portion 4b. In other words, positions of the respective transmission coils indicate discrete positions of the insertion portion 4b. The insertion shape image generation unit 35 generates an insertion shape image corresponding to an outline shape of the insertion portion 4b by interpolating the discrete position. Note that the insertion shape image is obtained in the measurement coordinate system.

The insertion shape image generation unit 35 gives the generated insertion shape image to the control unit 31. The control unit 31 generates display data based on the insertion shape image, and outputs the display data to the transmission unit 36. The transmission unit 36 transmits the display data to the video processor 9. The endoscope 4 gives the endoscope image of the inside of the body cavity, which is picked up by the image pickup device arranged at the distal end of the insertion portion 4b, to the video processor 9, and the video processor 9 outputs a combined image in which the endoscope image and the insertion shape image are combined to the monitor 5. In this way, the combined image of the endoscope image and the insertion shape image can be displayed on the display screen of the monitor 5.

The insertion length calculation unit 37 detects the coil at the anal position based on the output of the position detection unit 34, and calculates a length from the position of the coil to the distal end of the insertion portion 4b, as an insertion length. The insertion length calculation unit 37 gives information on the calculated insertion length to the communication unit 38, and the communication unit 38 transmits the insertion length information to the communication unit 19 of the image recording apparatus 10.

The control unit 11 of the image recording apparatus 10 causes the insertion length information retention unit 14 to receive and store the insertion length information received via the communication unit 19. The insertion length information is updated sequentially. In addition, the control unit 11 causes the image retention unit 12 to store the endoscope image outputted from the video processor 9. The control unit 11 supplies the endoscope image retained in the image retention unit 12, the time point information generated from the time point information generation unit 13, and the insertion length information retained in the insertion length information retention unit 14 to the recording data generation unit 15. The recording data generation unit 15 records the endoscope image and the insertion length information in association with each other using the time point information in the recording unit 16. For example, the recording data generation unit 15 generates an image file configured by the image data of the endoscope image and the metadata of the time point information and the insertion length information and gives the image file to the recording unit 16 for recording.

When the operator operates the operation portion (not shown) to instruct to play back the image file recorded in the recording unit 16, the control unit 11 instructs the playback unit 17 to play back the image file. The playback unit 17 reads out the image file recorded in the recording unit 16 and outputs the image file to the display control unit 18. The display control unit 18 receives the insertion length information included in the endoscope image and the metadata from the playback unit 17, and gives the image including the insertion length display based on the insertion length information and the endoscope image to the monitor 5. In this way, the endoscope image including the insertion length display is displayed on the display screen of the monitor 5.

The insertion length information indicates the insertion length of the insertion portion 4b of the endoscope 4 that acquires the endoscope image corresponding to the insertion length information. In other words, the insertion length information associated with the endoscope image at a predetermined recording time point indicates the insertion position, that is, the observation position at the predetermined time point. Accordingly, when the endoscope image and the insertion length display are displayed at the same time, the operator can easily recognize any insertion position (observation position) at which the endoscope image is picked up.

FIGS. 4, 5A, and 5B show examples in which an image is displayed on a display screen 5a of the monitor 5. In the display examples of FIGS. 4, 5A, and 5B, the endoscope image supplied to the image retention unit 12 is a combined image of the endoscope image and the insertion shape image. In each of the drawings, various displays regarding the insertion length are based on the played-back insertion length information.

In the example of FIG. 4, an endoscope image display region 41, an insertion shape image display region 42, and a status information display region 43 are provided on the display screen 5a by the display control unit 18. An endoscope image 41a is displayed in the endoscope image display region 41, and an insertion shape image 42a, a display 42b indicating that the subject P is in a supine position, and a bar display 42c indicating the insertion length are displayed in the insertion shape image display region 42. In addition, a date and recording time display 43a and an insertion length display 43b are displayed in the status information display region 43. From the insertion length display 43b, it can be seen that the endoscope image 41a is an image observed at a position inserted by 150 cm from the anus.

In the example of FIG. 5A, an endoscope image display region 51 and a status information display region 43 are provided on the display screen 5a by the display control unit 18. Further, an insertion shape image display region 52 is provided, as a sub screen, in the endoscope image display region 51. An endoscope image 51a is displayed in the endoscope image display region 51, and an insertion shape image 52a, a display 52b indicating that the subject P is in a supine position, and a bar display 52c indicating the insertion length are displayed on the sub screen in the insertion shape image display region 52. In addition, a date and recording time display 53a and an insertion length display 53b are displayed in the status information display region 53. From the insertion length display 53b, it can be seen that the endoscope image 51a is an image observed at a position inserted by 150 cm from the anus.

FIG. 5B shows an example in which an insertion shape image display region 55 is displayed to be superimposed on the endoscope image display region 51, the insertion shape image display region 55 being a pop-up of the insertion shape image display region 52 in FIG. 5A. For example, when the operator operates the operation portion (not shown), such a pop-up display can be performed. An enlarged insertion shape image 55a, a display 55b indicating that the subject P is in a supine position, and a bar display 55c indicating the insertion length are displayed in the insertion shape image display region 52.

As described above, according to the present embodiment, the insertion length information is recorded as metadata in association with the endoscope image. Thus, the insertion length display based on the insertion length information and the endoscope image are displayed at the same time during playback, and thus the operator can see the display of the monitor and can easily recognize at which observation site the displayed endoscope image is observed. Since the insertion length information is recorded as metadata, it is possible to easily search for the image part of the desired observation position in the endoscope image recorded as a moving image, using the insertion length information.

Second Embodiment

Figure 6:
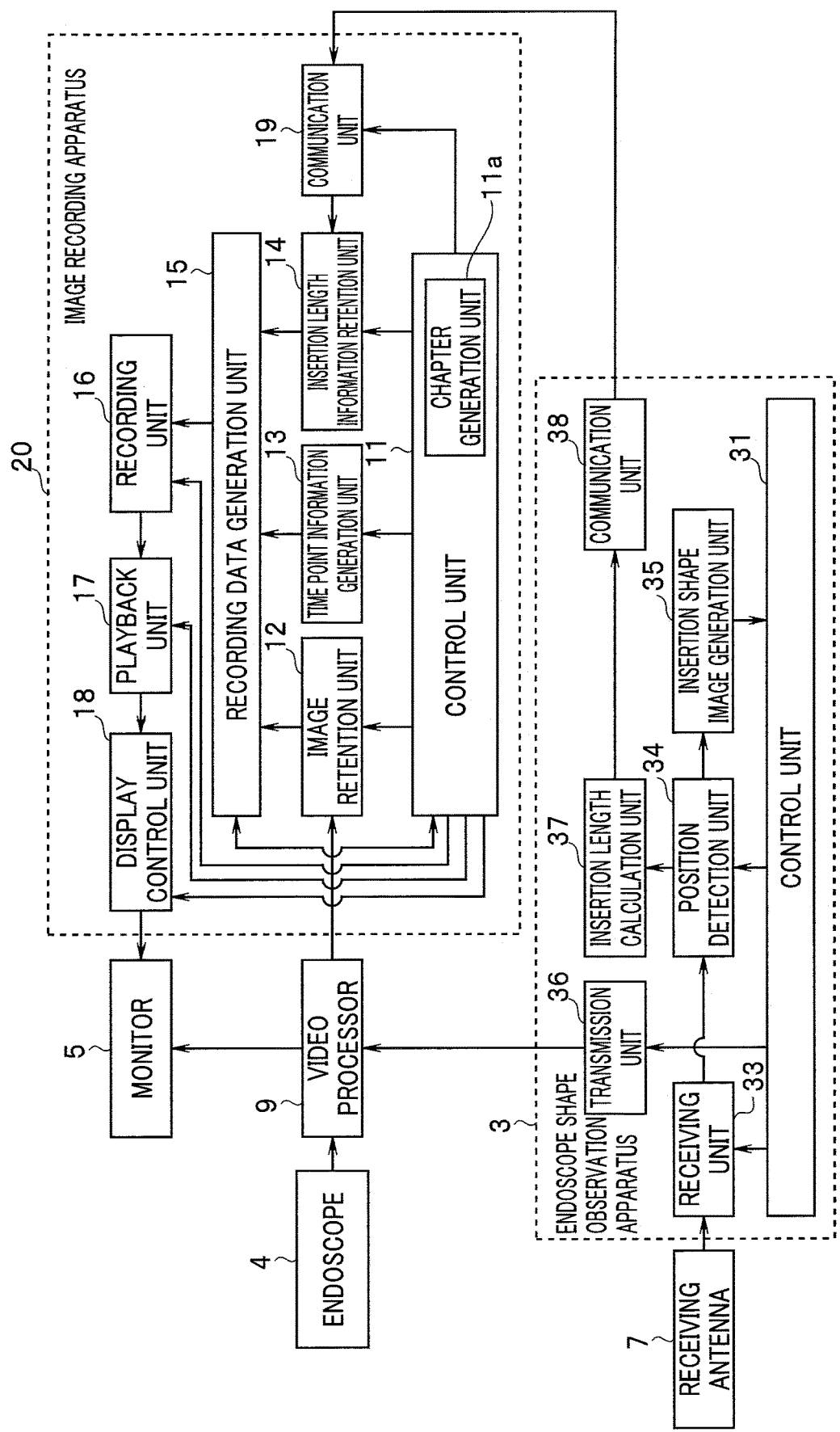
FIG. 6 is a block diagram showing a second embodiment of the present invention.

FIG. 6 is a block diagram showing a second embodiment of the present invention. In FIG. 6, the same components as the components in FIG. 1 are denoted by the same reference numerals, and will not be described. The present embodiment differs from the first embodiment in that an image recording apparatus 20 is used in which a chapter generation unit 11a is provided in the control unit 11. In the present embodiment, a chapter mark is added to the endoscope image (moving image) to be recorded.

The chapter generation unit 11a of the control unit 11 can add a chapter mark to the image file to be recorded, at a predetermined timing, by controlling the recording data generation unit 15. For example, the chapter generation unit 11a may be controlled to add a chapter mark to the image file at the timing of the operator's operation on the operation portion (not shown), or can also play back the recorded image file to read the insertion length information and to add a chapter mark according to the insertion length information.

For example, the chapter generation unit 11a can control the recording data generation unit 15 to read the insertion length information supplied from the insertion length information retention unit 14 to the recording data generation unit 15 during the recording of the endoscope image (moving image) (such a process not being shown) and to add a chapter mark to the image part of the endoscope image corresponding to a predetermined insertion length.

For example, the chapter generation unit 11a may add a chapter mark for each predetermined insertion length determined in advance. For example, the chapter generation unit 11a may add a chapter mark when the distal end portion of the insertion portion 4b reaches the anal position, that is, at the start of insertion and the end of removal of the insertion portion 4b.

Further, the chapter generation unit 11a may add a chapter mark when the insertion portion 4b inserted from the anus reaches the cecum, that is, when the insertion length is maximized. For example, the chapter generation unit 11a can control the recording data generation unit 15 such that the image file read from the recording unit 16 is given from the playback unit 17 (such a process not being shown) and a chapter mark is added to an image part of the endoscope image associated with the insertion length information indicating the maximum insertion length.

Figure 7:
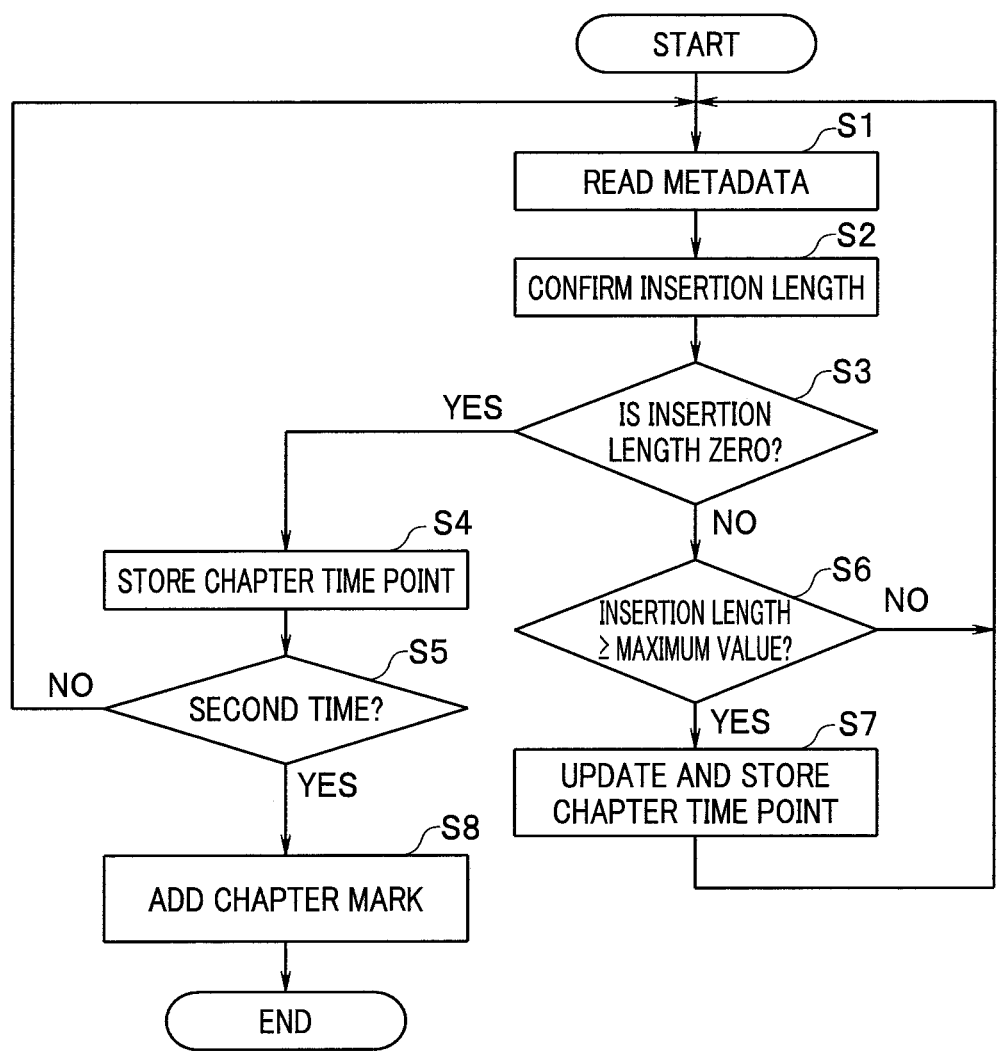
FIG. 7 is a flowchart showing an example of an operation flow adopted in the second embodiment.

An operation of the embodiment configured in this way will be described below with reference to FIGS. 7 and 8. FIG. 7 is a flowchart showing an example of an operation flow adopted in the second embodiment, and FIG. 8 is an explanatory diagram illustrating the operation of the embodiment.

In step S1 of FIG. 7, the chapter generation unit 11a sequentially reads the image data recorded in the recording unit 16, for example, from the metadata at the start of recording in order of time point, and confirms the insertion length obtained from the insertion length information (step S2).

Figure 8:
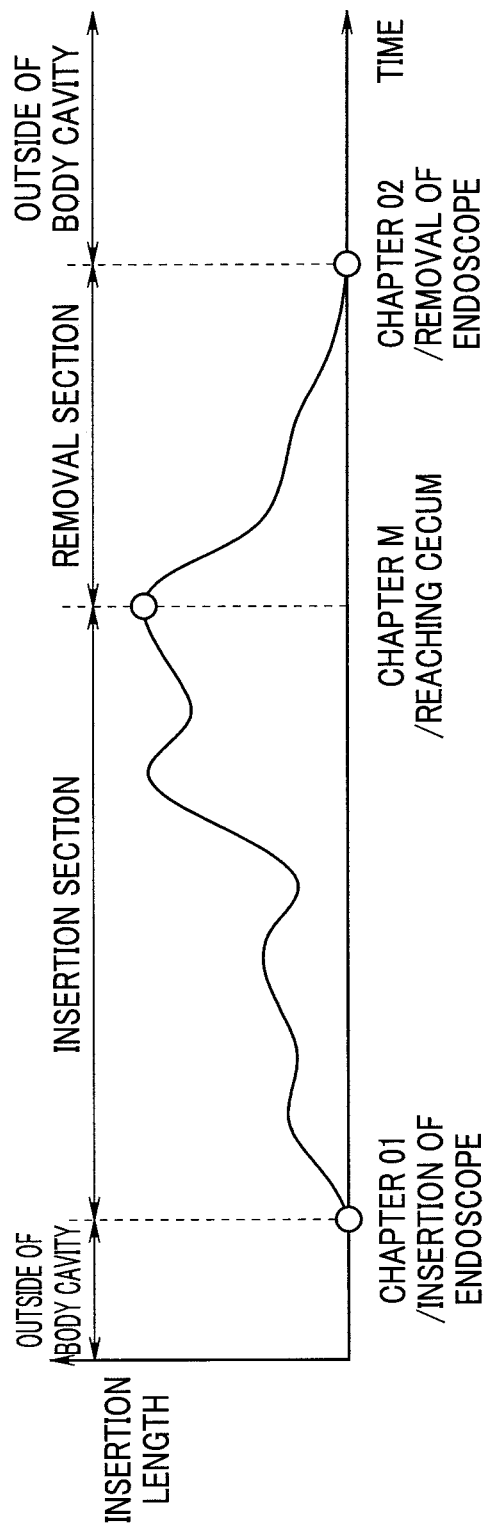
FIG. 8 is an explanatory diagram illustrating an operation of the second embodiment.

FIG. 8 shows a recording time of the endoscope image in a horizontal axis, and shows a change in the insertion length based on the insertion length information recorded in association with the recording time. Before the insertion portion 4b is inserted, that is, when the distal end portion of the insertion portion 4b is located outside the body cavity, the insertion length is not detected and the insertion length becomes zero (0) at the start of insertion. In step S3, the chapter generation unit 11a determines whether the insertion length, which is sequentially confirmed from the start of recording, becomes zero (0). When the insertion is started and the insertion length becomes zero (0), the chapter generation unit 11a shifts the process to step S4, and stores a time point corresponding to a timing when the insertion length is zero (0) in a memory (not shown), as a chapter time point of insertion length 0. In step S5, the chapter generation unit 11a determines whether the chapter time point of the insertion length 0 is stored for a second time. Since the chapter time point is stored for the first time at the start of insertion, the chapter generation unit 11a returns the process to step S1 and reads next insertion length information.

When the insertion portion 4b is inserted, the insertion length gradually increases. In step S3, when determining that the insertion length is not zero (0), the chapter generation unit 11a shifts the process to step S6 and determines whether the insertion length confirmed at the current time point is equal to or greater than the insertion length confirmed up to the previous time point, that is, whether the insertion length greater than or equal to the maximum value of the confirmed insertion length is confirmed. When the insertion is performed, the insertion length gradually increases, so that the chapter generation unit 11a shifts the process to step S7, updates the time point (chapter time point), at which the maximum insertion length is obtained, to store the time point in the memory (not shown), and then returns the process to step S1.

Thereafter, the same operation is repeated, the maximum value of the insertion length is updated during the period during which the insertion is being performed, and the chapter time point is updated and stored in step S7. Even before the distal end portion of the insertion portion 4b reaches the cecum, the insertion portion 4b may be retracted and inserted and the insertion length may be shortened in some cases. However, the insertion length is maximum when the distal end portion of the insertion portion 4b finally reaches the cecum. In the example of FIG. 8, the insertion length becomes maximum twice. It indicates that the insertion portion 4b is pulled out after the distal end portion of the insertion portion 4b reaches the cecum once, and then inserted again and the distal end portion of the insertion portion 4b reaches the cecum. In step S7, a time when the distal end portion of the insertion portion 4b finally reaches the cecum is stored as the chapter time point.

When the operator starts removing the insertion portion 4b, the insertion length gradually becomes a small value, and the insertion length becomes zero (0) when the distal end of the insertion portion 4b reaches the anus. Thus, the chapter generation unit 11a records a second chapter time point indicating the insertion length 0 in step S4. When performing the storage in step S4 twice, the chapter generation unit 11a adds a chapter mark in next step S8 corresponding to the chapter time point stored in steps S4 and S7. In other words, the chapter generation unit 11a controls the recording data generation unit 15 to record the chapter mark as metadata of the recording position corresponding to the chapter time point in the image data recorded in the recording unit 16.

In the example of FIG. 8, a chapter 01 is added corresponding to a time when the distal end of the insertion portion 4b reaches the anus from the outside of the body cavity and the insertion is started. In addition, a chapter M is added corresponding to a time when the distal end of the insertion portion 4b reaches the cecum, the insertion section ends, and the removal section starts. Further, a chapter 02 is added corresponding to a time when the distal end of the insertion portion 4b is removed from the anus and the removal section ends. In other words, the chapter generation unit 11a can discriminate respective medical scenes, for example, the outside of the body cavity, an insertion scene, and a removal scene by detecting that the insertion length is 0 and the final maximum value is 0 and can specify sections of the respective scenes by the chapter mark. Accordingly, it is possible to search for the playback image and to edit the respective scene using the chapter mark, for example.

As described above, according to the present embodiment, it is possible to automatically add the chapter mark to the image data according to the insertion length. Therefore, it is possible to easily search for the endoscope image at the observation position having a predetermined insertion length using the chapter mark. For example, it is possible to search for the endoscope image at a predetermined observation position using the playback apparatus having a function of jumping to the image part of the chapter mark. In addition, even at the time of editing, it is possible to easily perform the editing work using the chapter mark.

Third Embodiment

Figure 9:
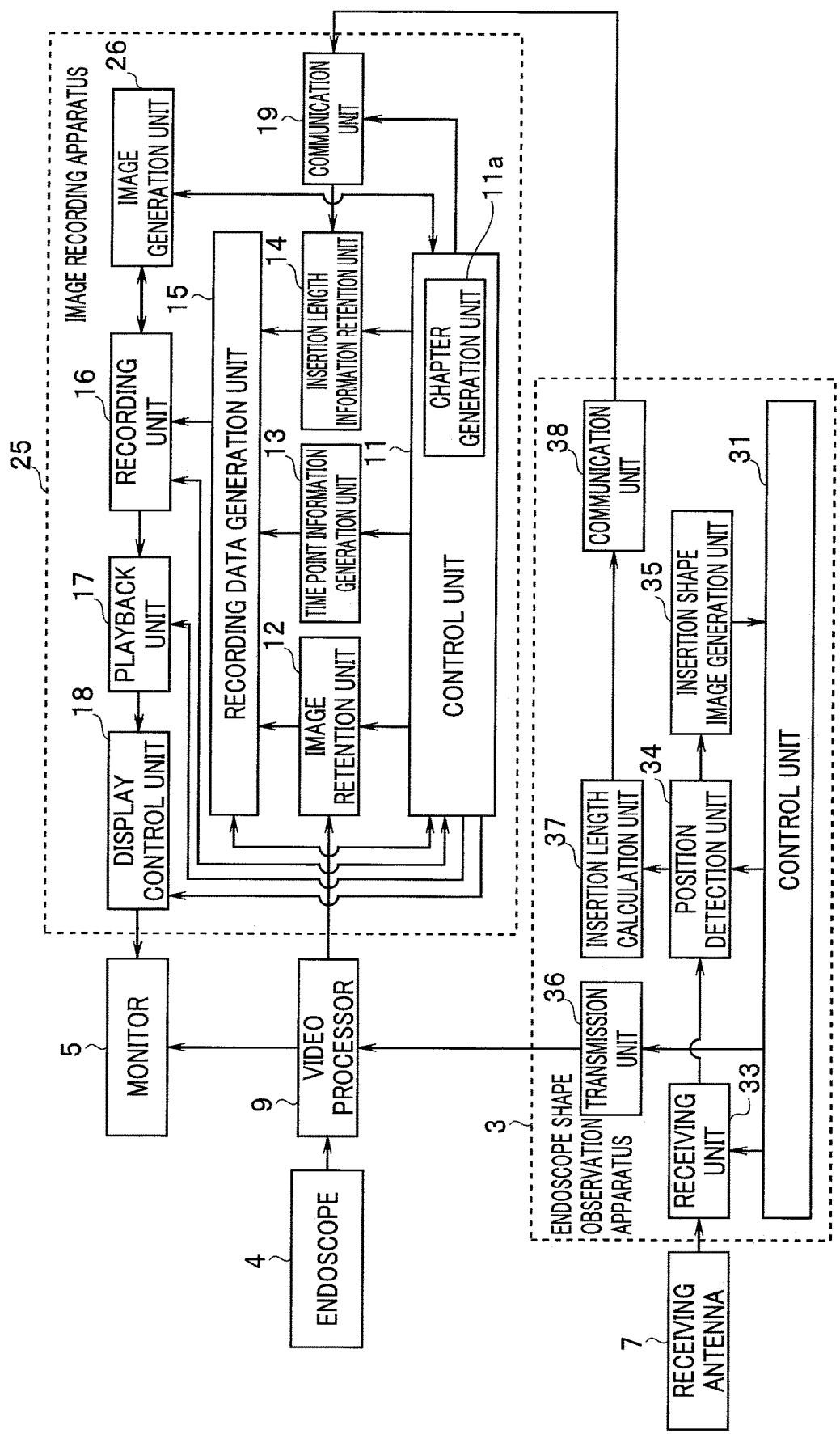
FIG. 9 is a block diagram showing a third embodiment of the present invention.

FIG. 9 is a block diagram showing a third embodiment of the present invention. In FIG. 9, the same components as the components in FIG. 6 are denoted by the same reference numerals and will not be described. According to the present embodiment, the recorded endoscope moving image can be automatically edited.

The present embodiment differs from the second embodiment in that an image recording apparatus 25 further including an image generation unit 26, which is an image generation apparatus, is used instead of the image recording apparatus 20. The image generation unit 26 is controlled by the control unit 11 to generate a moving image for saving in which the image recorded in the recording unit 16 is used as a master image and the master image is edited, for example, a moving image for saving in which an image quality of the master image is adjusted. The moving image for saving generated by the image generation unit 26 is recorded in the recording unit 16.

Figure 10:
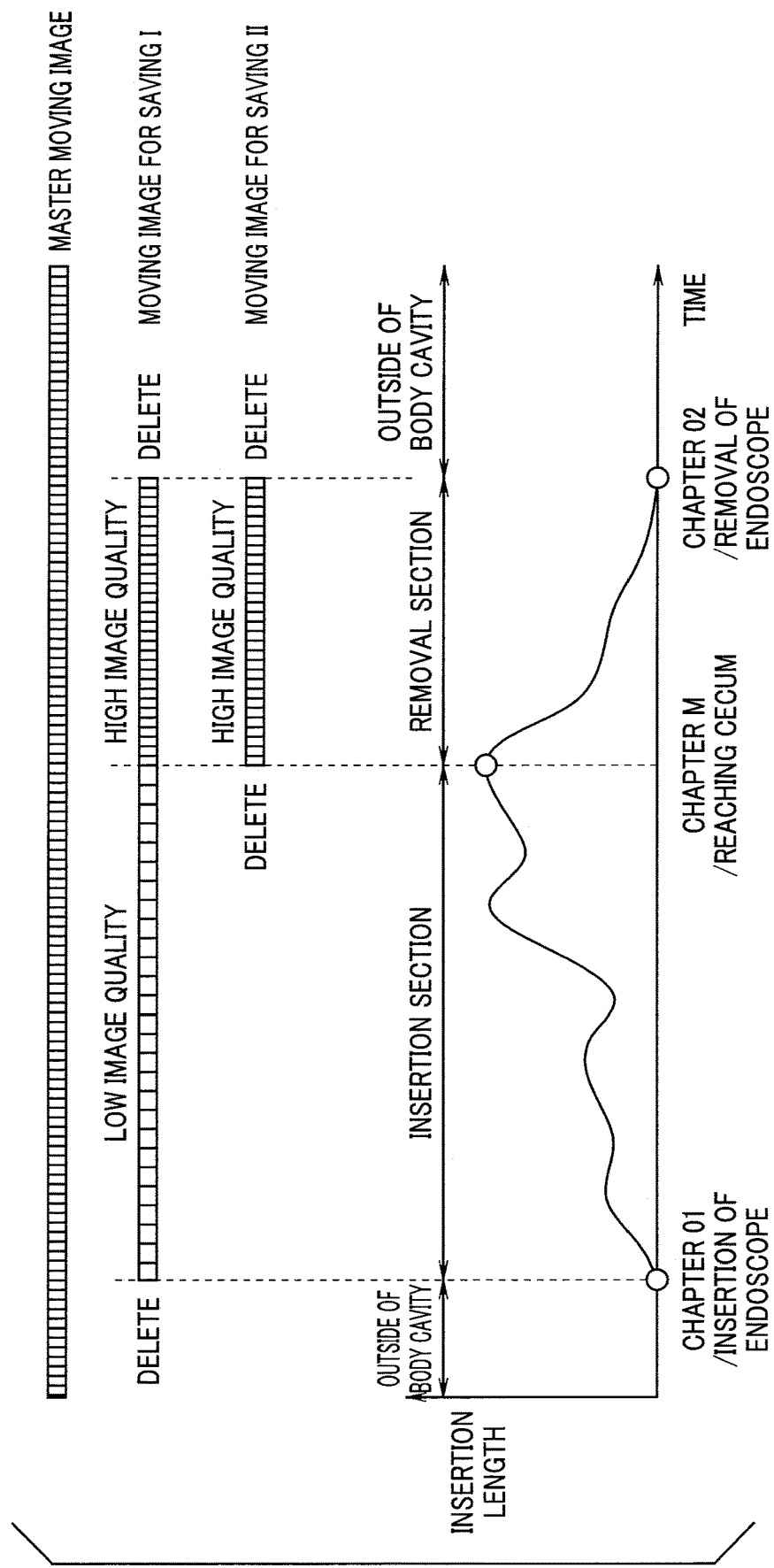
FIG. 10 is an explanatory diagram illustrating a moving image for saving generated by an image generation unit 26.

An operation of the embodiment configured in this way will be described below with reference to FIG. 10. FIG. 10 is an explanatory diagram illustrating the moving image for saving generated by the image generation unit 26. In FIG. 10, a lower part shows a change in the insertion length of the endoscope image at respective recording times using the same method as in FIG. 8, and an upper part shows a recording state of the moving image recorded in the recording unit 16.

An uppermost part in FIG. 10 shows a period during which a master moving image is recorded. In other words, the endoscope 4 starts recording from a state where the distal end of the insertion portion 4b is located outside the body cavity, and picks up an image during a whole period until a state where the distal end of the insertion portion 4b is removed and is located outside the body cavity from the insertion section and the removal section of the insertion portion 4b. The video processor 9 gives the endoscope image picked up during whole period to the image recording apparatus 25, and the recording data generation unit 15 records a moving image of the whole period in the recording unit 16, as a master moving image. In a subsequent editing, the video processor 9 generates a predetermined high-quality moving image as a master moving image such that moving images having various image quality can be generated. A hatching with a relatively narrow interval indicating a recording period of the master moving image in FIG. 10 indicates that the recording is performed with high image quality.

By the way, in consideration of the use of the recorded moving image, it is considered that the image part outside the body cavity is not necessary. In addition, an important image part in a large intestine examination is a removal section from the time of reaching the cecum to the end of removal. Therefore, it is considered to create a moving image for saving using a chapter mark, in consideration of the image quality of such sections.

The chapter generation unit 11a adds, to the recorded image, chapter marks of a chapter 01 indicating an image part at the start of endoscope insertion, a chapter M indicating an image part at a time when the insertion portion 4b reaches the cecum, and a chapter 02 indicating an image part at the end of removal of the endoscope.

The control unit 11 controls the image generation unit 26 according to information on the chapter mark to create two moving images for saving I and II from the master moving image. In other words, the image generation unit 26 deletes, from the master moving image, an image part during a period from the start of recording to the chapter 01 and an image part from the chapter 02 to the end of recording, and generates a moving image for saving I in which an image part from the chapter 01 to the chapter M is converted with low image quality. The moving image for saving I in FIG. 10 shows the recording period, and indicates that recording with low image quality is performed by relatively coarse hatching. Since an insertion scene is not a very important scene and is recorded with low image quality, a required capacity can be reduced.

Further, the image generation unit 26 generates a moving image for saving II in which the image part during the period from the start of recording to the chapter M and the image part from the chapter 02 to the end of recording are deleted from the master moving image. The moving image for saving II in FIG. 10 shows the recording period, and indicates that only the removal section is recorded with relatively high image quality. In other words, the removal scene, which is important for examination, is saved with high image quality, so that observation is more easily performed.

Although the example is described in which the control unit 11 determines the medical scene based on the information on the chapter mark and sets the image quality of the moving image for saving, the control unit 11 may be configured to determine the medical scene based on the insertion length information and to set the image quality of the moving image for saving. For example, the control unit 11 may control the image generation unit 26 to record a high-quality image from the time when the maximum insertion length is finally obtained to the time when the removal is completed, for example, the time when the insertion length becomes 0.

As described above, according to the present embodiment, it is possible to automatically generate the moving image for saving in which the master moving image recorded with high image quality during the whole period of the endoscope examination is edited according to the insertion length. It is possible to perform an editing process, for example, a process of deleting the image pickup portion of the outside the body cavity and a process of recording only an important examination portion with high image quality. In this way, it is possible to automate complicated editing work and easily generate a moving image suitable for use.

Fourth Embodiment

Figure 11:
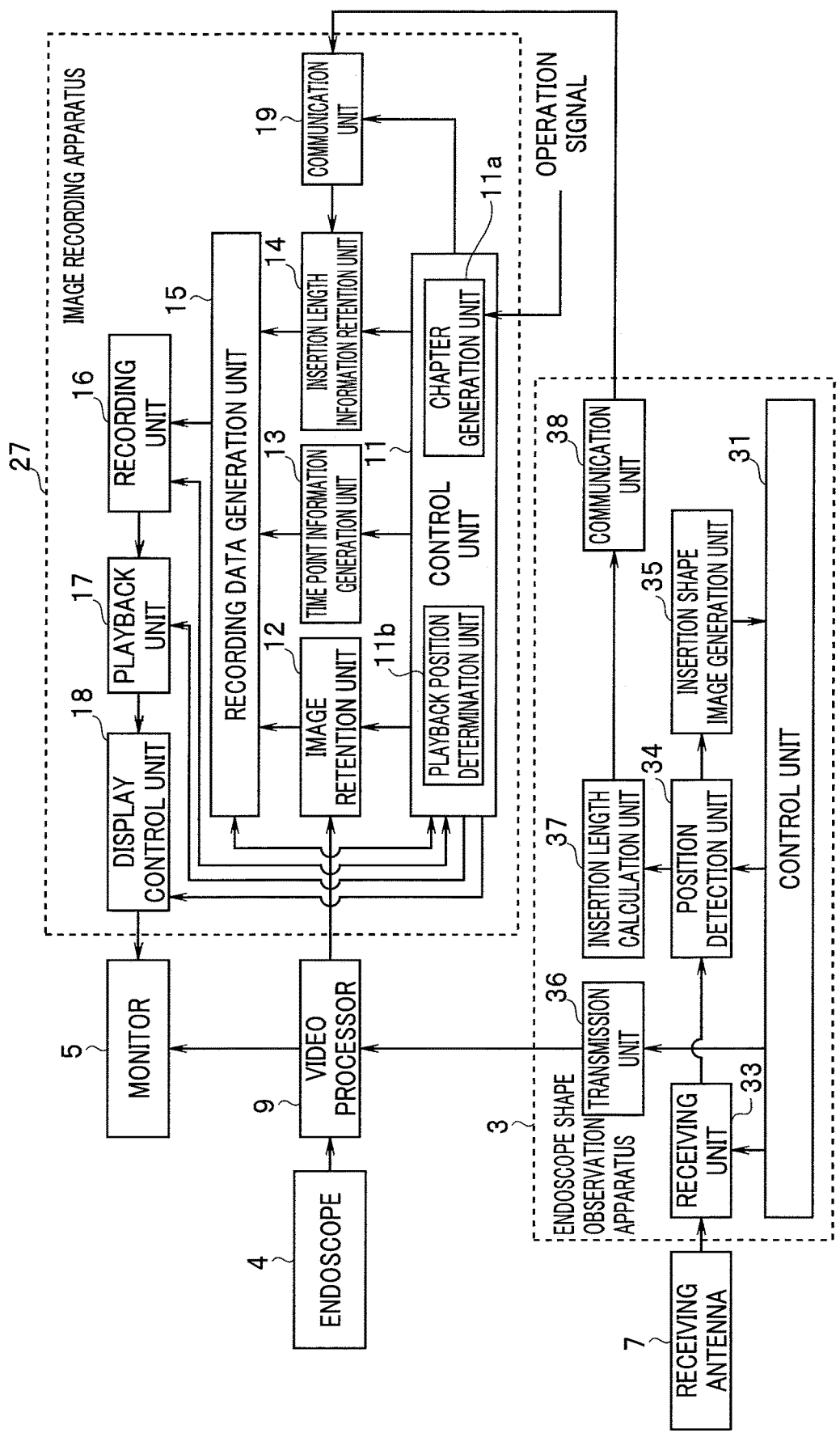
FIG. 11 is a block diagram showing a fourth embodiment of the present invention.

FIG. 11 is a block diagram showing a fourth embodiment of the present invention. In FIG. 11, the same components as the components in FIG. 6 are denoted by the same reference numerals and will not be described. According to the present embodiment, comparison with past medical case records of the same patient at the time of follow-up observation is easily performed.

The present embodiment differs from the second embodiment in that an image recording apparatus 27, in which the control unit 11 further includes a playback position determination unit 11b, is used instead of the image recording apparatus 20. Insertion length information is given to the playback position determination unit 11b from the insertion length information retention unit 14. The playback position determination unit 11b is configured to supply the insertion length information given from the insertion length information retention unit 14 to the playback unit 17, as information for designating a playback position. The playback unit 17 reads out image data from the recording unit 16 based on the information supplied from the playback position determination unit 11b. In other words, the playback unit 17 refers to the metadata in the image file recorded in the recording unit 16 to read and play back the image data of the image part which matches the insertion length information designated by the playback position determination unit 11b or is associated with the insertion length information having a value within a predetermined threshold value.

When the image recorded in the recording unit 16 includes an image part of an insertion section and a removal section, image parts having the same insertion length are provided at two or more locations. In this case, since it is conceivable that treatment will be performed at the time of removal, the playback unit 17 should play back image data having the same or similar insertion length in the removal section in consideration of follow-up observation.

The playback unit 17 outputs the played-back image data and metadata to the display control unit 18. The display control unit 18 generates a combined image based on the inputted image data and metadata, and outputs the combined image to the monitor 5. In addition, an endoscope image is also given to the monitor 5 from the video processor 9. The video processor 9 can also output the endoscope image including an insertion length display.

Figure 12:
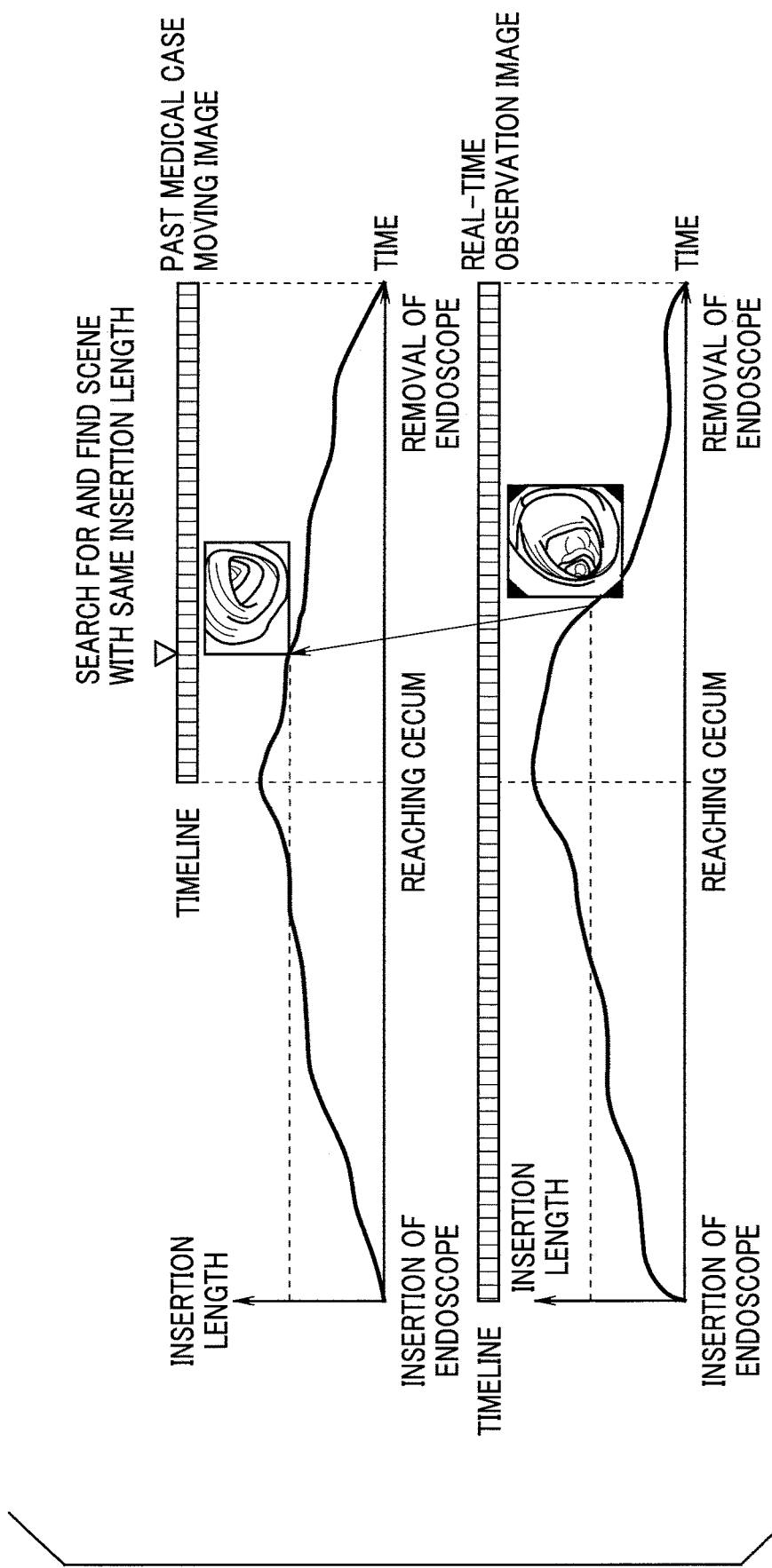
FIG. 12 is an explanatory diagram showing a change in insertion length of an endoscope image at respective recording times using the same method as in FIG. 8.

An operation of the embodiment configured in this way will be described below with reference to FIGS. 12 and 13. FIG. 12 is an explanatory diagram showing a change in the insertion length of the endoscope image at respective recording times using the same method as in FIG. 8, and an upper part and a lower part show an example of a past medical case moving image and a current observation moving image of the same subject, respectively. Further, FIG. 13 is an explanatory diagram showing an example in which an image is displayed on the monitor 5.

Now, it is assumed that the follow-up observation of the subject P is performed. It is assumed that a past medical case moving image of the subject P subjected to the follow-up observation is recorded in the recording unit 16. In other words, image data using time point information and insertion length information as metadata is recorded in the recording unit 16 as a medical case moving image. A chapter mark may not be added to the medical case moving image.

The operator starts to pick up an endoscope image with the endoscope 4, and inserts the insertion portion 4b from the anus of the subject P. An image pickup signal is supplied to the video processor 9 from the endoscope 4. In addition, the insertion length calculation unit 37 of the endoscope shape observation apparatus 3 calculates an insertion length of the insertion portion 4b. Information on the insertion length is supplied to the video processor 9, and the video processor 9 outputs an endoscope image including the insertion length display to the monitor 5. Further, the insertion length information is given to the insertion length information retention unit 14 via the communication unit 19 of the image recording apparatus 27 from the endoscope shape observation apparatus 3.

In the present embodiment, the playback position determination unit 11b of the control unit 11 reads the insertion length information from the insertion length information retention unit 14, and outputs the read insertion length information to the playback unit 17, as information for designating a playback position. The playback unit 17 reads the insertion length information of the recording unit 16, and reads and plays back image data of an image part that matches or approximates the insertion length information designated from the playback position determination unit 11b. The playback unit 17 outputs the read image data and related metadata to the display control unit 18. The display control unit 18 adds an insertion length display to the endoscope image played back by the playback unit 17 and outputs the combined image to the monitor 5.

The insertion length information retained in the insertion length information retention unit 14 changes according to the insertion/removal operation of the insertion portion 4b from the operator. The image part, which is played back by the playback unit 17, of the recording 16 also changes according to the change in the insertion length, and the past image part at the observation position corresponding to the observation position (insertion position) currently being observed is read and played back from the recording unit 16. In other words, the past image from the display control unit 18 and the current image from the video processor 9 are the past image and the current observation image of the same subject P at the same observation position, respectively. The monitor 5 simultaneously displays the past image and the current observation image on the display screen 5a.

In FIG. 12, the lower part shows the change in insertion length corresponding to the endoscope image currently being observed. It is considered that the change in insertion length at the time of the current observation shown in the lower part of FIG. 12 is different from the change in insertion length at the time of recording of the past medical moving image shown in the upper part of FIG. 12 and the examination times are also different from each other. However, in the present embodiment, the current observation image and the past medical case image are displayed at the same time depending on the insertion length regardless of the recording time of the image. An image 61a at the insertion length shown by a broken line in the lower part of FIG. 12 and an image 62a at the same insertion length shown by a broken line in the upper part of FIG. 12 are the past and current images of the same subject at the same observation position, respectively.

When the operator inserts and removes the insertion portion 4b, the current observation position changes and the image changes, and the past image outputted from the image recording apparatus 27 also changes to the image at the observation position corresponding to the current observation position at the same time. Accordingly, the operator can always determine the current state from the observation image by comparison with the past image of the same subject at the same observation position, which is extremely useful for the follow-up observation.

FIG. 13 shows a display of the monitor 5 in this case. On the display screen 5a of the monitor 5, a display region 61 for the current observation image is provided on a left side, and a display region 62 for the past medical case image is provided on a right side. In the display region 61, an endoscope image 61a currently being observed and a status information display 61b are displayed. The status information display 61b indicates that the endoscope image 61a is picked up at 14:04 on Mar. 14, 2018 and the observation position is a position with an insertion length of 100 cm.

In the display region 62, an endoscope image 62a, which is the past medical case image, and a status information display 62b are displayed. The status information display 62b indicates that the endoscope image 62a is picked up at 15:03 on Feb. 14, 2015 and the observation position is a position with an insertion length of 100 cm. It is indicated that a chapter mark C is set in an image part corresponding to the insertion length. In addition, the status information displays 61b and 62b can also be turned off.

As described above, according to the present embodiment, since the playback position of the recorded past medical case image can be set according to the insertion length at the time of the current observation, the past medical case image at the same observation position as the current observation position can be simultaneously displayed together with the current observation image. The operator can compare the current image with the past image of the same subject at the same observation position without designation of a complicated playback position or the like, which is extremely useful for the follow-up observation.

Note that the current observation image can also be recorded in the recording unit 16 as metadata in association with the insertion length information. Therefore, the example of determining the playback position of the past medical case image according to the current observation position is described above, but the playback position of the currently recorded observation image can also be determined based on the observation position (insertion position) of the past observation image.

(Modification)

The example is described above in which the playback position determination unit 11b designates the playback position of the recording unit 16 based on the insertion length information of the current observation image, but the current observation position to be observed with the follow-up observation can also be designated based on the past medical case image.

The playback position determination unit 11b of the control unit 11 may be configured to perform switching between a first mode for designating the playback position of the past medical case record based on the insertion length information corresponding to the image currently being observed and a second mode for designating the playback position based on the insertion length information corresponding to the chapter mark in the past medical case record. For example, it is conceivable that the chapter generation unit 11*a* sets the chapter mark at the site subjected to treatment (insertion position) according to the operation signal based on the operation of the operator during the past observation. In this case, the second mode may be set at the time of follow-up observation.

FIG. 14 is an explanatory diagram showing a change in the insertion length of the endoscope image at respective recording times using the same method as in FIG. 8. In the example of FIG. 14, a chapter mark Amin indicating the insertion length 0 at the start of insertion, a chapter mark Amin' indicating the insertion length 0 at the end of removal, a chapter mark Bmax' at the time of reaching the cecum where the maximum insertion length is finally obtained, and a chapter mark Bmax at the time of reaching the cecum where the maximum insertion length is obtained for the first time are automatically given. Further, the example of FIG. 14 indicates that a chapter mark C is manually set at an observation position (insertion position) where the operator finds a polyp.

The chapter generation unit 11*a* records the chapter mark in the recording unit 16, as metadata, in association with the image data. The playback position determination unit 11*b* reads the chapter mark from the recording unit 16 and outputs the chapter mark to the playback unit 17 as information for designating the playback position. The playback unit 17 plays back the image part and the metadata corresponding to the designated chapter mark and outputs the image part and the metadata to the display control unit 18.

In this way, the display control unit 18 can output the endoscope image including the insertion length display at the designated chapter mark position to the monitor 5.

On the display screen 5*a* of the monitor 5, an endoscope image at the position of the chapter mark C is displayed, for example, as in the display region 62 of the display example of FIG. 13. An insertion length display indicating that the insertion length is 100 cm is displayed in the display region 62, and the operator may insert and remove the insertion portion 4*b* with reference to the insertion length display such that the insertion length of the endoscope image in the display region 61 is 100 cm. In this way, it is possible to designate the previously treated site with the chapter mark, and to easily compare the past medical case image and the current observation image at the treated site with each other.

As described above, according to the modification, a desired position of the past medical case image can be played back by addition of the chapter mark at an arbitrary position of the recorded image. Since the insertion length display is displayed based on the insertion length information at the playback position set by the chapter mark, the operator can simply recognize how much the insertion portion should be inserted or removed in order to observe the observation position of the treated site, which is extremely useful for the follow-up observation.

The example is described in the modification in which the playback position is designated by the chapter mark, but the insertion length can also be directly designated to set the playback position. In this case, the playback position can be designated regardless of the presence or absence of the chapter mark.

The present invention is not limited to each of the embodiments described above as it is, and at the implementation state, the components can be modified and embodied without departing from the gist of the invention. In addition, various inventions can be formed by appropriate combination of the plurality of components disclosed in each of the above-described embodiments. For example, some components of all the components shown in the embodiments may be deleted. Further, the components described in different embodiments may be combined as appropriate.

What is claimed is:

1. A medical system comprising:
a first processor comprising hardware, the first processor being configured to:
receive a first moving image data, wherein the first moving image data includes a first endoscope image data at a first time point,
receive a first data from a second processor, the first data indicating a first length of an endoscope inserted into a body cavity at the first time point;
determine whether the first length is equal to a predetermined length;
in response to the determining that the first length is equal to the predetermined length, record the first time point as a first chapter time point;
determine whether a number of times of determining that an insertion length of the endoscope inserted into the body cavity is equal to the predetermined length is twice; and
in response to the determining that the number of times is twice, add a first chapter mark based on the first chapter time point.

2. The medical system according to claim 1, wherein the first moving image data further includes a second endoscope image data at a second time point being after the first time point, and
the first processor is further configured to:
receive a second data from the second processor, and the second data indicating a second length of the endoscope inserted into the body cavity at the second time point;
determine whether the second length is equal to the predetermined length; and
in response to the determining that the second length is equal to the predetermined length, record the first second time point as a second chapter time point.

3. The medical system according to claim 2, wherein the first processor is further configured to:
in response to the determining that the number of times is twice, add a second chapter mark based on the second chapter time point.

4. The medical system according to claim 3, wherein the second chapter mark is added to the second endoscope image data as metadata.

5. The medical system according to claim 2, wherein the first processor is further configured to generate a second moving image data based on the first moving image data.

6. The medical system according to claim 5, wherein the second moving image data does not include images that are obtained before the first time point and after the second time point.

7. The medical system according to claim 2, wherein
the first moving image data includes a third endoscope image data at a third time point, the third time point being before the second time point and after the first time point, and
the first processor is configured to:
record the first length as a maximum length;
record the first time point as a third chapter time point;

receive a third data from the second processor, the third data indicating a third length of the endoscope inserted into the body cavity at the third time point;

determine whether the third length is equal to the predetermined length;

in response to determining that the third length is not equal to the predetermined length, determine whether the third length is equal to or greater than the maximum length; and in response to determining that the third length is equal to or greater than the maximum length, update the maximum length as the third length and update the third time point as the third chapter time point.

8. The medical system according to claim 7, wherein the first processor is configured to add a third chapter mark to the third endoscope image data.

9. The medical system according to claim 8, wherein the first processor is configured to generate a second moving image data including images obtained before the second time point and after the third time point based on the first moving image data.

10. The medical system according to claim 2, further comprising:
the endoscope including:
an insertion portion inserted into the body cavity; and
an image pickup device configured to output an image signal of the body cavity; and
a video processor configured to generate the first endoscope image data and the second endoscope image data based on the output image signal;
the second processor being configured to:
acquire information on the insertion length data when the insertion portion of the endoscope is inserted into a subject; and
generate the first data and the second data based on the acquired information.

11. The medical system according to claim 1, wherein the first chapter mark corresponds to a start of insertion of an insertion portion of the endoscope, and a second chapter mark corresponds to an end of removal of the endoscope).

12. The medical system according to claim 1, wherein the first processor is further configured to:
generate a display image based on the first endoscope image data with the first data; and
output the generated display image to a display.

13. The medical system according to claim 12, wherein the display image further includes a real time endoscope image picked up from the endoscope.

14. The medical system according to claim 12, further comprising the display configured to display the generated display image.

15. The medical system according to claim 1, wherein the first processor is configured to:
in response to determining that the first length is not equal to the predetermined length, determine whether the first length is equal to or greater than a maximum length of the endoscope inserted into the body cavity; and
in response to determining that the first length is equal to or greater than the maximum length, update the maximum length as the first length and update a chapter time point as the first time point.

16. The medical system according to claim 15, wherein the first processor is configured to add a third chapter mark to the first endoscope image data.

17. The medical system according to claim 1, wherein the first processor is configured to:
receive an insertion shape image of the endoscope from the second processor.

18. The medical system according to claim 1, wherein the first processor is configured to add the first chapter mark on the first endoscope image data by an instruction from a user.

19. The medical system according to claim 1, wherein the first chapter mark is added to the first endoscope image data as metadata.

20. A method of controlling a medical system comprising:
receiving a first data acquired at a first time point, wherein the first data indicates a first length of an endoscope inserted into a body cavity;
receiving a first moving image data including a first endoscope image data acquired at the first time point;
determining whether the first length is equal to a predetermined length;
in response to the determining that the first length is equal to the predetermined length, recording the first endoscope image data in association with the first data
determining whether a number of times of determining that an insertion length of the endoscope inserted into the body cavity is equal to the predetermined length is twice; and
in response to the determining that the number of times is twice, adding a first chapter mark based on a first chapter time point.

* * * * *